(12) United States Patent
Ostroot et al.

(10) Patent No.: US 12,251,158 B2
(45) Date of Patent: Mar. 18, 2025

(54) TISSUE ABLATION USING A MEDICAL DEVICE

(71) Applicant: BOSTON SCIENTIFIC SCIMED, INC., Maple Grove, MN (US)

(72) Inventors: Timothy A. Ostroot, Cokato, MN (US); John A. Zanussi, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 146 days.

(21) Appl. No.: 16/913,804

(22) Filed: Jun. 26, 2020

(65) Prior Publication Data

US 2020/0405386 A1   Dec. 31, 2020

Related U.S. Application Data

(60) Provisional application No. 62/868,620, filed on Jun. 28, 2019.

(51) Int. Cl.
*A61B 18/14* (2006.01)
*A61B 18/00* (2006.01)
*A61B 18/12* (2006.01)

(52) U.S. Cl.
CPC .. *A61B 18/1492* (2013.01); *A61B 2018/0016* (2013.01); *A61B 2018/00577* (2013.01);
(Continued)

(58) Field of Classification Search
CPC ...... A61B 18/1492; A61B 2018/00577; A61B 2018/1467; A61B 2018/0016;
(Continued)

(56) References Cited

U.S. PATENT DOCUMENTS 5,891,136 A   4/1999   McGee et al.
6,814,730 B2   11/2004   Li
(Continued)

FOREIGN PATENT DOCUMENTS

WO   2006044794 A2   4/2006

OTHER PUBLICATIONS

Invite to to Pay Additional Fees dated Oct. 6, 2020 for International Application No. PCTUS2020039936.

*Primary Examiner* — Thomas A Giuliani
*Assistant Examiner* — Abigail M Ziegler
(74) *Attorney, Agent, or Firm* — Seager, Tufte & Wickhem, LLP

(57) ABSTRACT

An example medical device is disclosed. The medical device includes a catheter shaft including a distal end portion, wherein the distal end portion includes an ablation assembly. The ablation assembly includes an expandable frame including a base, an end region and a plurality of struts extending between the base and the end region, the struts defining a plurality of apertures along the frame. The ablation assembly also includes an electrical circuit coupled to an inner surface of the second end region of the frame, the electrical circuit including a plurality of ablation electrodes coupled thereto. Further, the expandable frame is designed to shift from a delivery configuration in which the ablation electrodes face inward from the inner surface of the expandable frame to an expanded configuration in which the ablation electrodes face away from the base of the expandable frame.

20 Claims, 14 Drawing Sheets

(52) U.S. Cl.
CPC . *A61B 2018/126* (2013.01); *A61B 2018/1467* (2013.01); *A61B 2018/1475* (2013.01)

(58) Field of Classification Search
CPC .. A61B 2018/00267; A61B 2018/1475; A61B 5/283; A61B 5/287; A61B 5/6852; A61B 5/6859; A61B 5/6874
See application file for complete search history.

(56) References Cited

U.S. PATENT DOCUMENTS

| | | | |
|---|---|---|---|
| 8,202,269 B2 * | 6/2012 | Wolf, Jr. | A61B 18/082 606/49 |
| 8,834,461 B2 | 9/2014 | Werneth et al. | |
| 9,179,963 B2 | 11/2015 | Ben-Ezra et al. | |
| 10,130,420 B2 * | 11/2018 | Basu | A61B 18/1492 |
| 10,327,658 B2 * | 6/2019 | Basu | A61B 5/287 |
| 10,772,655 B2 * | 9/2020 | Rem-Bronneberg | A61B 17/320016 |
| 2013/0096550 A1 | 7/2013 | Hill | |
| 2013/0331831 A1 * | 12/2013 | Werneth | A61B 18/18 606/41 |
| 2014/0200578 A1 | 7/2014 | Groff et al. | |
| 2017/0100187 A1 | 4/2017 | Basu et al. | |
| 2018/0193078 A1 | 7/2018 | Rajagopalan et al. | |
| 2019/0314083 A1 * | 10/2019 | Herrera | A61B 5/6859 |

\* cited by examiner

TISSUE ABLATION USING A MEDICAL DEVICE

CROSS-REFERENCE TO RELATED APPLICATIONS

This application claims the benefit of priority of U.S. Provisional Application No. 62/868,620 filed Jun. 28, 2019, the entire disclosure of which is hereby incorporated by reference.

TECHNICAL FIELD

The present disclosure pertains to medical devices, and methods for manufacturing medical devices. More particularly, the present disclosure pertains to tissue diagnosis and/or ablation.

BACKGROUND

A wide variety of intracorporeal medical devices have been developed for medical use, for example, intravascular use. Some of these devices include ablation catheters, ablation devices, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a catheter shaft including a distal end portion, wherein the distal end portion includes an ablation assembly. The ablation assembly includes an expandable frame including a base, an end region and a plurality of struts extending between the base and the end region, the struts defining a plurality of apertures along the frame. The ablation assembly also includes an electrical circuit coupled to an inner surface of the second end region of the frame, the electrical circuit including a plurality of ablation electrodes coupled thereto. Further, the expandable frame is designed to shift from a delivery configuration in which the ablation electrodes face inward from the inner surface of the expandable frame to an expanded configuration in which the ablation electrodes face away from the base of the expandable frame.

Alternatively or additionally, wherein the electrical circuit includes a flex circuit.

Alternatively or additionally, wherein the flex circuit includes a plurality of leaflets, and wherein each of the plurality of leaflets includes one or more ablation electrodes.

Alternatively or additionally, wherein the flex circuit includes a plurality of fold lines, and wherein each of the fold lines extends from a perimeter of the flex circuit to a center portion of the flex circuit.

Alternatively or additionally, wherein each of the leaflets is separated by one of the plurality of fold lines.

Alternatively or additionally, wherein the flex circuit unfolds along one or more of the fold lines when the expandable frame shifts from the delivery configuration to the expanded configuration.

Alternatively or additionally, wherein the flex circuit includes a diameter when in the expanded configuration, and wherein the diameter is between 10 mm and 45 mm.

Alternatively or additionally, wherein the flex circuit is designed to shift from the expanded configuration to the delivery configuration, and wherein the flex circuit folds inward along the fold lines when shifting from the expanded configuration to the delivery configuration.

Alternatively or additionally, wherein the flex circuit includes a pocket formed therein, and wherein at least a portion of the expandable frame is designed to insert into the pocket.

Alternatively or additionally, wherein the ablation electrodes are designed to ablate tissue utilizing ablation processes selected from the group comprising hypothermic ablation, hyperthermic ablation and athermal ablation.

Alternatively or additionally, wherein the flex circuit forms a continuous surface when in the expanded configuration.

Alternatively or additionally, wherein the flex circuit is configured to span across two or more apertures of the frame when in the expanded configuration.

Another example medical device includes a catheter shaft including a distal end portion and an expandable scaffold coupled to the distal end portion of the catheter shaft, the scaffold having a first end region and a second end region, wherein the scaffold includes a plurality of struts extending between the first end region and the second end region, the struts defining a plurality of apertures along the scaffold. The medical device also includes an ablation pad coupled to the second end region of the scaffold, the ablation pad including a plurality of ablation electrodes coupled thereto. Further, the expandable scaffold is designed to shift from a delivery configuration in which at least a portion of the ablation pad is disposed along an inner surface of the expandable scaffold to an expanded configuration in which the ablation pad faces a target tissue site.

Alternatively or additionally, wherein the ablation pad includes a flex circuit.

Alternatively or additionally, wherein the ablation pad includes a plurality of fold lines, and wherein each of the fold lines extends from a perimeter of the ablation pad to a center portion of the ablation pad.

Alternatively or additionally, wherein the ablation pad unfolds along one or more of the fold lines when the expandable scaffold shifts from the delivery configuration to the expanded configuration.

Alternatively or additionally, wherein the ablation pad forms a continuous surface when in the expanded configuration.

Alternatively or additionally, wherein the first end region is substantially perpendicular to the second end region when in the expanded configuration.

An example method of ablating tissue includes advancing an ablation catheter to a target tissue site, the ablation catheter including a catheter shaft including a distal end portion. The ablation catheter also includes an expandable frame including a base, an end region and a plurality of struts extending between the base and the end region, the struts defining a plurality of apertures along the frame. The ablation catheter also includes a flexible electric circuit coupled to an inner surface of the second end region of the frame, the flexible electric circuit including a plurality of ablation electrodes coupled thereto. Further, the method also includes shifting the frame from a delivery configuration in which the ablation electrodes face inward from the inner surface of the expandable frame to an expanded configuration in which the ablation electrodes face away from the base of the expandable frame.

Alternatively or additionally, the method further comprising advancing the expandable frame such that the ablation electrodes contact the target tissue.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
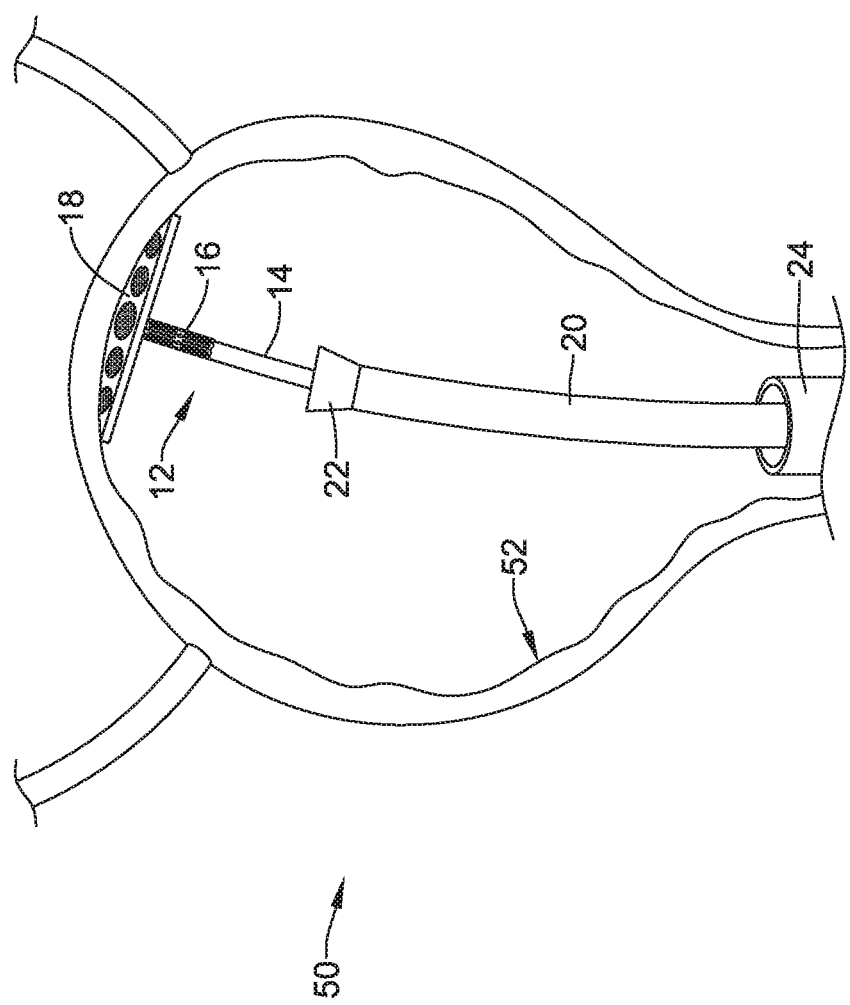
FIG. 1 is a plan view of an example medical device positioned in a bladder.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Ablation therapy is a minimally invasive procedure that may be used to destroy abnormal tissue that occurs with a variety of medical conditions. For example, a physician might use an ablation procedure to treat an abnormal cardiac arrhythmia, tissue abnormalities or kidney disease. In other examples, a physician may utilize ablation therapy to treat bladder cancer. One technique that may be utilized to treat abnormal tissue pathologies may include ablation of tissue substrates contributing to the abnormal tissue pathology. Ablation processes including, but not limited to, cold (e.g., hypothermic ablation), heat (e.g., hyperthermic ablation), High Voltage Discharge/IRE (e.g., athermal ablation), chemicals and/or other means of creating a lesion in the tissue substrate may isolate diseased tissue from normal tissue. In some instances, ablation therapy may involve locating the tissue contributing to the abnormal tissue pathology using a mapping and/or diagnosing catheter, followed by using one or more ablation electrodes to destroy and/or isolate the diseased tissue.

Prior to performing an ablation procedure, a physician may utilize specialized mapping and/or diagnostic catheters to precisely locate tissue contributing and/or causing the abnormal tissue pathology. It is often desirable to precisely locate the targeted tissue prior to performing an ablation procedure to effectively alleviate and/or eliminate the abnormal tissue pathology. After locating the targeted tissue site, a physician may utilize a specialized ablation catheter to ablate the target tissue.

Further, in some instances it may be desirable to utilize and incorporate one or more flat electrodes into the distal portion of an ablation device. For example, some of the medical devices disclosed herein may include utilizing a relatively flat flex circuit coupled to an expandable framework, whereby the medical device may be designed to permit the physician to customize the ablation pattern utilized to treat the target tissue.

FIG. 1 is a schematic view of an ablation device 12 which may be utilized to access and treat a targeted tissue region in the body. Specifically, FIG. 1 generally shows the system 12 deployed along the inner surface 52 of a bladder 50. However, this is not intended to be limiting. Rather, it can be appreciated the ablation device 12 may be utilized in other regions of the body. For example, while the illustrated embodiment shows the system 12 being used for treating the bladder, the system 12 (and the methods described herein) may alternatively be configured for use in other tissue applications, such as procedures for treating tissue in the heart, prostate, colon, stomach, throat, esophagus, intestine, pancreas, lung, gall bladder, uterus, nerves, and other regions of the body, including body regions not typically accessed by a catheter.

As illustrated in FIG. 1, in some instances the ablation device 12 may be delivered to a target tissue site via one or more delivery catheters. For example, FIG. 1 illustrates that the ablation device 12 may be advanced through the lumen of a delivery sheath 20. The delivery sheath 20 may be utilized to both deliver and/or retrieve the ablation device 12. For example, the ablation device 12 may be advanced through the lumen of the delivery sheath 20 in a collapsed configuration. Further, the ablation device 12 may be advanced out the distal end of the delivery sheath 20, whereby the ablation device 12 may shift from a collapsed configuration to an expanded configuration.

Additionally, it can be appreciated that the delivery sheath 20 may be utilized to retrieve the ablation device 12 after an ablation procedure is completed. For example, after completion of an ablation procedure, a physician may retract the ablation device 12 in a distal-to-proximal direction into the distal end of the delivery sheath 20. FIG. 1 illustrates that the delivery sheath 20 may include a tapered distal end 22. It can be appreciated that the tapered end 22 of the delivery sheath 20 may include one or more reinforcement elements (e.g., reinforcement members, stiffening members, etc.) designed to funnel the ablation device 12 into the lumen of the delivery sheath 20.

In some instances, both the delivery sheath 20 and the ablation device 12 may be delivered to a target tissue site via an access sheath 24. The access sheath 24 may include one or more lumens extending therein designed to permit the delivery sheath 20 and/or the ablation device 12 to be advanced therethrough. For example, in some instances the access sheath 24 may be a guide catheter, steerable guide catheter, guide sheath, introducer sheath, endoscope, cystoscope, bronchoscope, gastroscope or the like, any of which may include a working channel designed to permit the delivery sheath 20 and/or the ablation device 12 to be advanced therethrough.

FIG. 1 further illustrates that the ablation device 12 may include a shaft 14 having a proximal end portion and a distal end portion. The shaft 14 may be defined as a tubular member including lumen extending therein. In other words, the shaft 14 may include a lumen which extends along the entire length of the shaft 14 or the lumen may extend along only a portion of the shaft 14. The lumen of the shaft 14 may be sized and/or shaped to accommodate a guidewire, tubular member, shaft (e.g., a push/pull member) or the like to extend therein. However, in other instances, the shaft 14 may not include a lumen extending therein. For example, the shaft 14 may be a solid member.

FIG. 1 further illustrates that the shaft 14 may include an expandable frame 16 (e.g., scaffold, stent, etc.) coupled to the distal end of the shaft 14. The expandable frame 16 may be formed (e.g., laser cut) from a metallic (e.g., Nitinol) tube. For example, in some instances the expandable frame 16 may be defined as a self-expanding shape memory scaffold. However, it is contemplated that the expandable frame 16 may be constructed from materials other than Nitinol. For example, the expandable frame 16 may be constructed from alternative metals, polymeric and/or ceramic materials and combinations thereof. It is also contemplated that, in some examples, the expandable frame 16 made be formed as a braided structure. For example, the frame 16 may be formed from a braided Nitinol.

Additionally, FIG. 1 illustrates that the ablation device 12 may include an electrical circuit 18 (e.g., flex circuit, ablation pad, etc.) coupled to a portion of the expandable frame 16. As will be described in greater detail below, the electrical circuit 18 may include one or more ablation electrodes coupled to a polymeric material, whereby the electrical circuit is designed to attach and span a portion or the entirety of the inner surface of the expandable frame 16.

As described above, in some examples the shaft 14 of the ablation device 12 may include a lumen through which a "push/pull" shaft may extend. In some examples, a distal end region of the push/pull shaft may be coupled to the electrical circuit 18. Further, actuation of the push/pull shaft may change the shape and/or configuration of the electrical circuit 18. For example, advancing the push/pull shaft in a proximal-to-distal direction may push the central region of the electrical circuit 18 toward tissue, thereby shifting the electrical circuit 18 from a collapsed configuration to a convex configuration (as shown in FIG. 1). The push/pull member and its relationship to the ablation device 12 is further discussed below with respect to FIG. 8 and FIG. 10.

While not shown in FIG. 1, the proximal portion of the shaft 14 may include a hub member and an electrical connector attached thereto. In some examples, the hub member may include an electrical connector. The hub member may also include a lumen and/or passage extending therethrough which substantially aligns with the lumen of the shaft 14. Further, the hub member may include one or more features designed to control the deployment and recovery of the flex circuit (via actuation of a push/pull member, for example). Similar to that described with respect to the shaft 14, it can be appreciated that the lumen of the hub may be sized and/or shaped to accommodate a guidewire and/or a push/pull member extending therethrough. It can be further appreciated that the hub may include one or more features which advance and/or retrieve the ablation device out of or into the delivery sheath 20, respectively.

Figure 2:
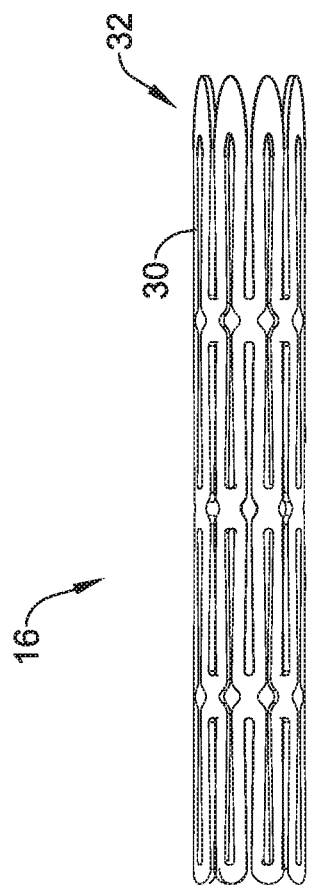
FIG. 2 illustrates a portion of an example medical device in an unexpanded configuration.

FIG. 2 illustrates the expandable frame 16 shown in FIG. 1 in a collapsed (e.g., a delivery, pre-deployment, etc.) configuration. It is noted that, for simplicity purposes, the electrical circuit 18 described above has been omitted.

As shown in FIG. 2, the expandable frame 16 may include one or more strut members 30 arranged to form a scaffold. As will be described in greater detail below, the strut members 30 may be arranged to form a scaffold having a variety of the patterns, shapes, geometries, etc. Additionally, it can be appreciated that the strut members 30 may generally be arranged such that the frame 16 may be defined as extending completely around (e.g., 360 degrees) the outer surface of the shaft 14. Additionally, FIG. 2 illustrates that the distal end of the frame 16 may include one or more peaks 32 arranged around the longitudinal axis of the frame 16. As illustrated in FIG. 2, the peaks 32 may be formed by tapering one or more of the strut members 30 in a proximal-to-distal direction. In some examples, the distal end region of each of the peaks 32 may be rounded or other atraumatic shape.

Figure 3:
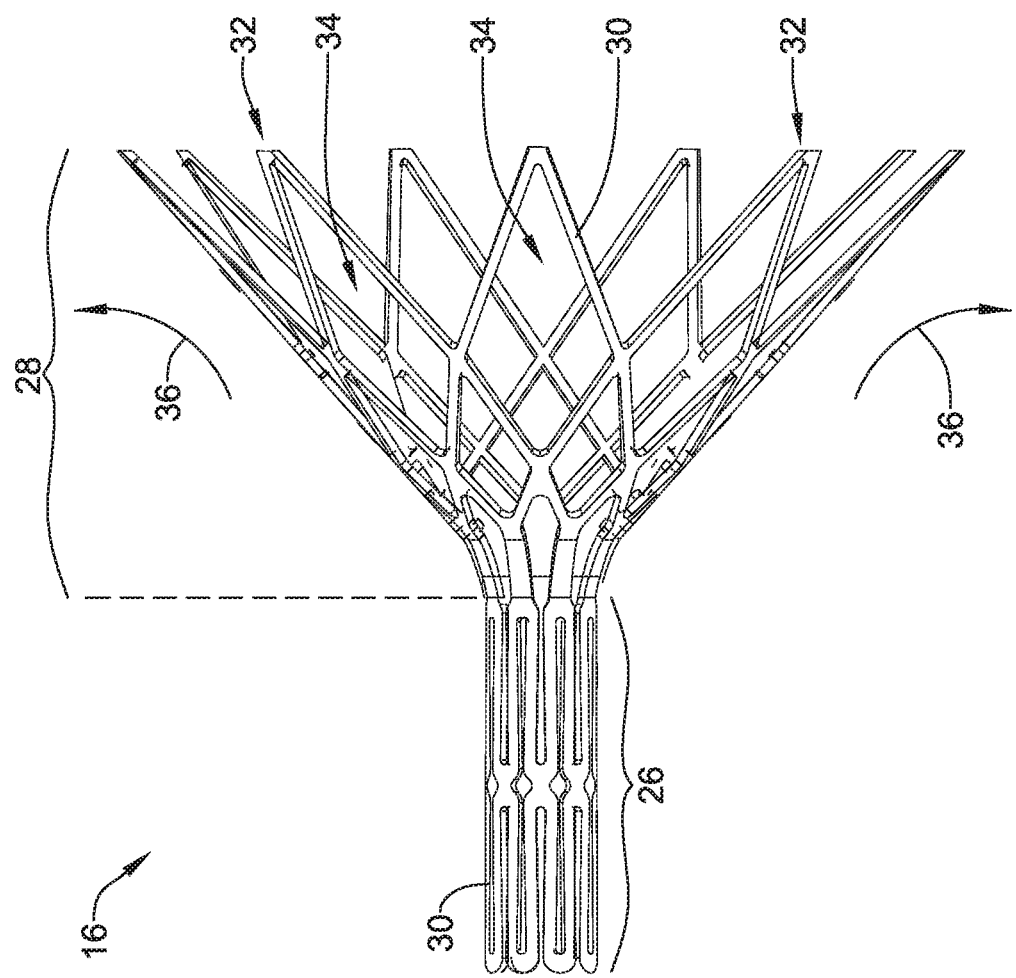
FIG. 3 illustrates a portion of the example medical device shown in FIG. 2 in a partially deployed configuration.

FIG. 3 illustrates the expandable frame 16 shown in FIG. 2 in a partially deployed configuration. As shown in FIG. 3, the expandable frame 16 may include a base member 26 and an expandable portion 28. The base member 26 may be a portion (e.g., unitary member) of the tube (e.g., Nitinol tube) used to form the expandable frame 16 described above. Alternatively, it is contemplated that the base member 26 may be a distinct component attached separately to the expandable portion 28. For example, the base member 26 may be welded, joined, etc. to one or more strut members 30 defining the expandable portion 28. Additionally, the base member 26 may be attached to the distal end region of the shaft 14. In some examples, the strut members 30 of the expandable portion 28 may form a unitary structure with the base member 26. Further, the strut members 30 may extend between the base member 26 and the expandable portion 28 of the expandable frame 16.

FIG. 3 further illustrates that the expandable portion 28 of the expandable frame 16 may include one more apertures, openings, holes, etc. 34 defined by the geometric arrangement of the strut members 30. In some instances (such as that illustrated in FIG. 3), the apertures 34 may include a diamond shape. However, while FIG. 3 shows the frame 16 having apertures shaped generally as diamonds, it can be appreciated that the frame 16 may include a variety of shape, sizes, designs, arrangements, geometries, etc. Further, in some examples, the frame 16 may include a variety of shapes and/or geometric arrangements (e.g., squares, rectangles, circles, triangles, polygons, etc.). For example, while the above discussion has focused on the shape of the frame 16 shown in FIG. 3, it is not intended to be limiting. For example, the number, shape, configuration and/or arrangement of the strut members 30 and/or the apertures 34 may depend on the particular performance characteristics desired to be balanced within the frame 16. For example, additional strut members 30 may be added to the frame 16 to provide increased stiffness. In other instances, the strut members 30 may take on particular geometries that varies (e.g., adjusts) the functional performance of the frame 16.

Additionally, FIG. 3 shows the expandable portion 28 of the expandable frame 16 folding outward as illustrated by lines 36. It can be appreciated from FIG. 3 that as the expandable portion 28 expands, the distance between adjacent strut members 30 may increase, which, in turn, increases the size of the apertures 34.

Figure 4:
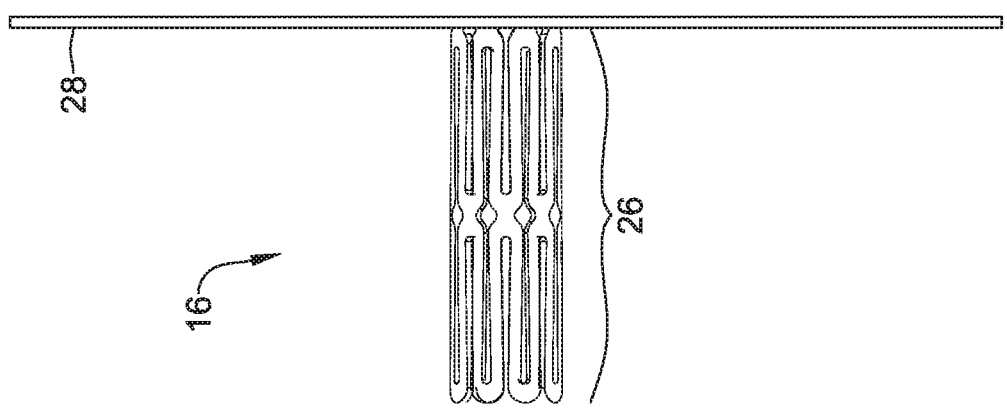
FIG. 4 illustrates a portion of the example medical device shown in FIG. 2 in a fully deployed configuration.

FIG. 4 illustrates the expandable member 16 (including the base member 26 and the expandable portion 28) after having been further expanded beyond the configuration illustrated in FIG. 3. For example, FIG. 4 illustrates that the expandable portion 28 may expand to an extent in which the expandable portion 28 is substantially flat. In other words, FIG. 4 illustrates that the expandable portion 28 may "unfold" to a position in which the expandable portion 28 is substantially flat and substantially perpendicular to the base member 26.

Figure 5:
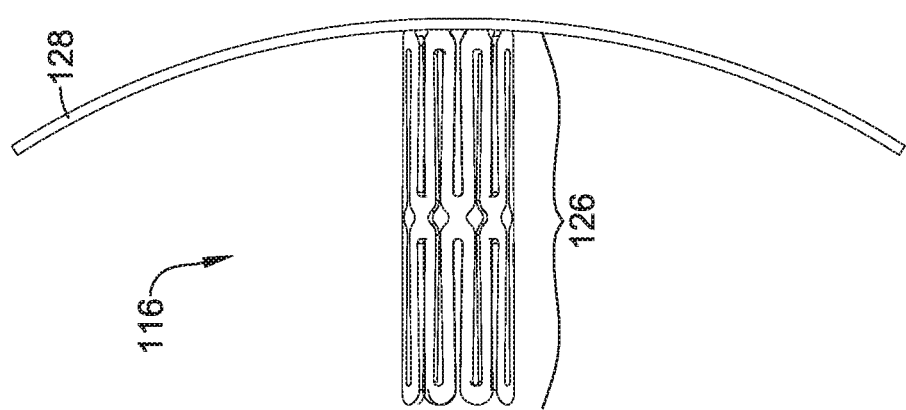
FIG. 5 illustrates another example medical device in a fully deployed configuration.

FIG. 5 illustrates another example expandable member 116 (including a base member 126 and an expandable portion 128). The expandable member 116, base member 126 and expandable portion 128 may be similar in form and function to the expandable member 16, base member 26 and expandable portion 28 described above. Like FIG. 4, FIG. 5 illustrates the expandable member 116 after having been expanded beyond the configuration illustrated in FIG. 3. For example, FIG. 5 illustrates that the expandable portion 128 may expand to an extent in which the expandable portion 128 "unfolds" to a substantially convex shape. In other words, FIG. 5 illustrates that the expandable portion 128 may "unfold" to a position in which the circumferential edge of the expandable portion 128 is positioned proximal of the distal end region of the base member 126.

Figure 6:
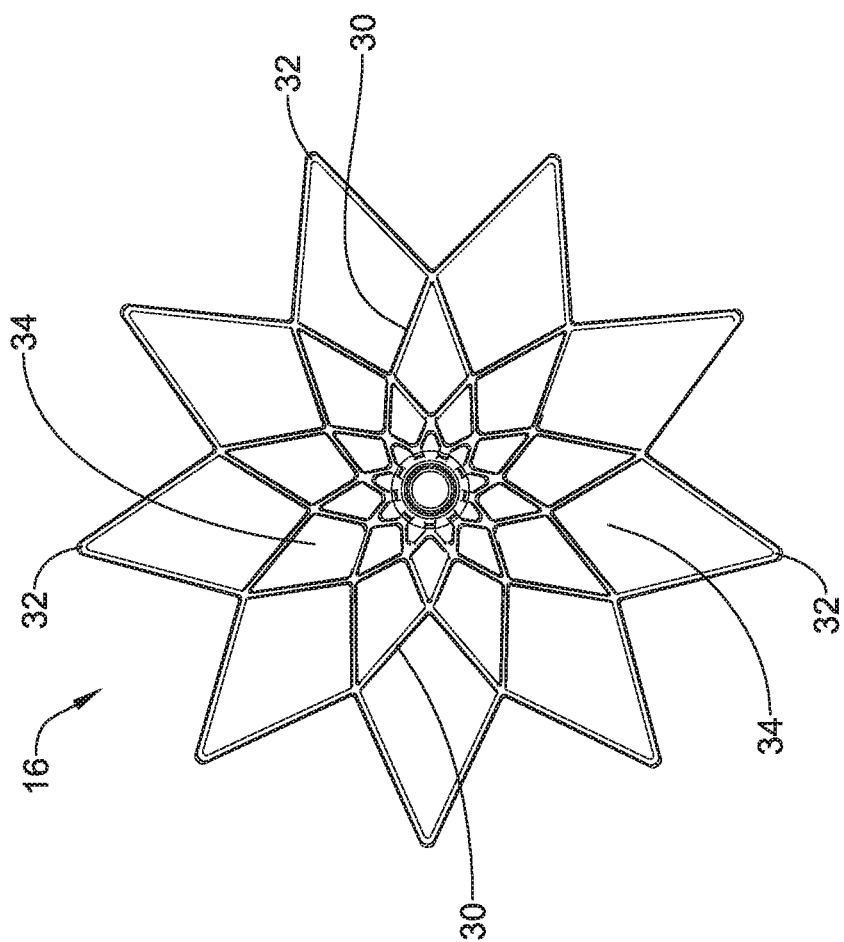
FIG. 6 illustrates an end view of an example medical device.

FIG. 6 is an end view of the example expandable frame 16 shown in FIGS. 2-6. As shown in FIG. 6, the struts 30 may be arranged such that they create generally diamond-shaped apertures 34. Further, it can be seen that the apertures 34 decrease in size when moving from the outer edge (e.g., outer circumference) to the center region of the frame 16.

These are only examples. As stated above, numerous geometries, patterns and covering design combinations are contemplated.

FIG. 6 further illustrates the peaks 32 arranged around the center region of the frame 16. As discussed above, the peaks 32 may be defined as tapered portions of the struts 30. It can be appreciated from FIG. 4, FIG. 5 and/or FIG. 6 that when the frame 16 is an expanded configuration, the peaks 32 may be directed (e.g., point) radially away from the longitudinal axis of the base member 26 (as shown in the flat shape of FIG. 4) or may be flexed outwardly and point in a distal-to-proximal direction (as shown in the convex shape of FIG. 5). Additionally, it can be appreciated from FIG. 6 that when the frame 16 is an expanded configuration, the inner surface of the frame 16 (as defined by the inner surface of the struts 30) may face outward. In other words, in the unexpanded configuration shown in FIG. 2 the inner surface of the struts 30 defining the frame 16 may face inward toward the longitudinal axis of the base member 26. However, when in the expanded configuration, strut members 30 may expand such that the inner surface of the struts 30 defining the frame 16 may face away from the base member 26. This feature may permit the inner surface of the struts 30 to face the tissue of a tissue target site.

Figure 7:
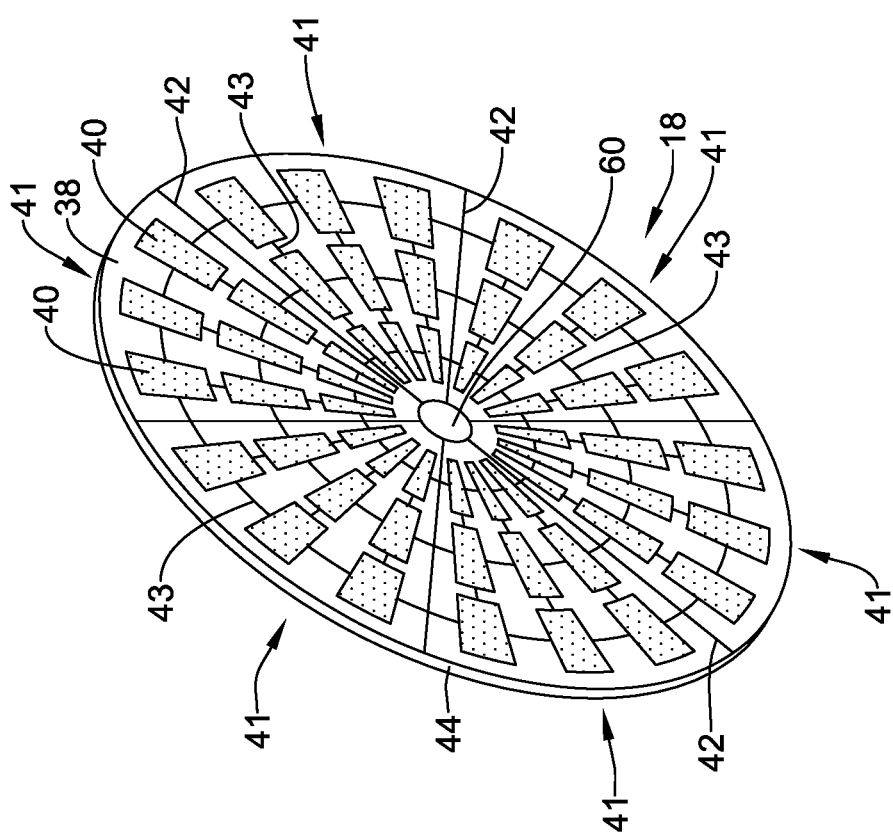
FIG. 7 illustrates a portion of an example medical device.

FIG. 7 illustrates an example ablation member 18 in an expanded configuration. In some instances, the ablation member 18 shown in FIG. 7 may be referred to as a flex circuit. In some examples, the ablation member 18 (e.g., flex circuit) may resemble a disc-shaped member or pad. However, this is not intended to be limiting. While FIG. 7 illustrates the ablation member 18 having a substantially circular shape, it is contemplated that the ablation member 18 may include a variety of other geometric shapes (e.g., squares, rectangles, squares, etc.).

Additionally, the ablation member 18 illustrated in FIG. 7 may include one or more ablation electrodes 40 coupled to one or more polymer substrates 38. In some instances, the ablation electrodes 40 may be positioned between (e.g., sandwiched) between two polymer substrates 38, whereby a portion of one of the polymer substrates 38 may be removed to permit the ablation electrodes 40 to directly contact target tissue.

FIG. 7 further illustrates that, in some examples, one or more of the ablation electrodes 40 may be grouped together in one or more "leaflets" (e.g., leaflets 41) which are separated by a fold line 42. For example, FIG. 7 illustrates each leaflet 41 including nine ablation electrodes 40 separated by a fold line 42. FIG. 7 illustrates each fold line 42 extending from a perimeter 44 of the ablation assembly 18 to a center region 60 of the ablation assembly 18. As will be discussed in greater detail below, the fold lines 42 may define those portions of the ablation assembly 18 which crease, fold, pleat, etc. as the ablation assembly 18 shifts from an unexpanded configuration to an expanded configuration.

While FIG. 7 illustrates each leaflet including nine individual ablation electrodes 40, this is not intended to be limiting. Rather, it is contemplated that the ablation electrodes 40 may be grouped in a variety of different configurations and/or arrangements. In other words, each leaflet may include more or less than nine individual ablation electrodes 40. Further, it is contemplated that each individual ablation electrode may include a variety of different shapes (e.g., circles, rectangles, triangles, ovals, squares, polygons, etc.).

Additionally, it is contemplated that the ablation member 18 may be formed from materials which may be substantially elastic. In other words, materials utilized to construct the polymer substrates 38 and/or the ablation electrodes 40 may be able to stretch or flex. It can further be appreciated that constructing the ablation member 18 from materials which are semi-compliant (e.g., elastic, flexible) may permit the ablation member 18 to expand and/or contract (e.g., fold) with greater efficiency as compared to an ablation member 18 constructed from more rigid materials.

Additionally, FIG. 7 illustrates that, in some examples, one or more of the ablation electrodes 40 may be electrically connected to one another via electrical wires 43 (e.g., "traces") and/or other similar electrical connections. Further, the electrical trace wires 43 may be coupled to signal wires (not shown in FIG. 7) which may be coupled to the handle member described above. It can be appreciated in examples where one or more of the ablation electrodes 40 are connected to one another via the electrical wires 43, the electrical wires 43 may be positioned between (e.g., sandwiched between) the one or more layers of the polymer substrates, as described above.

For all example electrodes discussed herein, it is contemplated that the electrodes may be operated in a variety of configurations. For example, in some instances one or more of the ablation electrodes 40 described herein may be operated in a bipolar configuration. Operating the electrodes 40 in a bipolar configuration may provide improved control, speed and/or efficiency.

Figure 8:
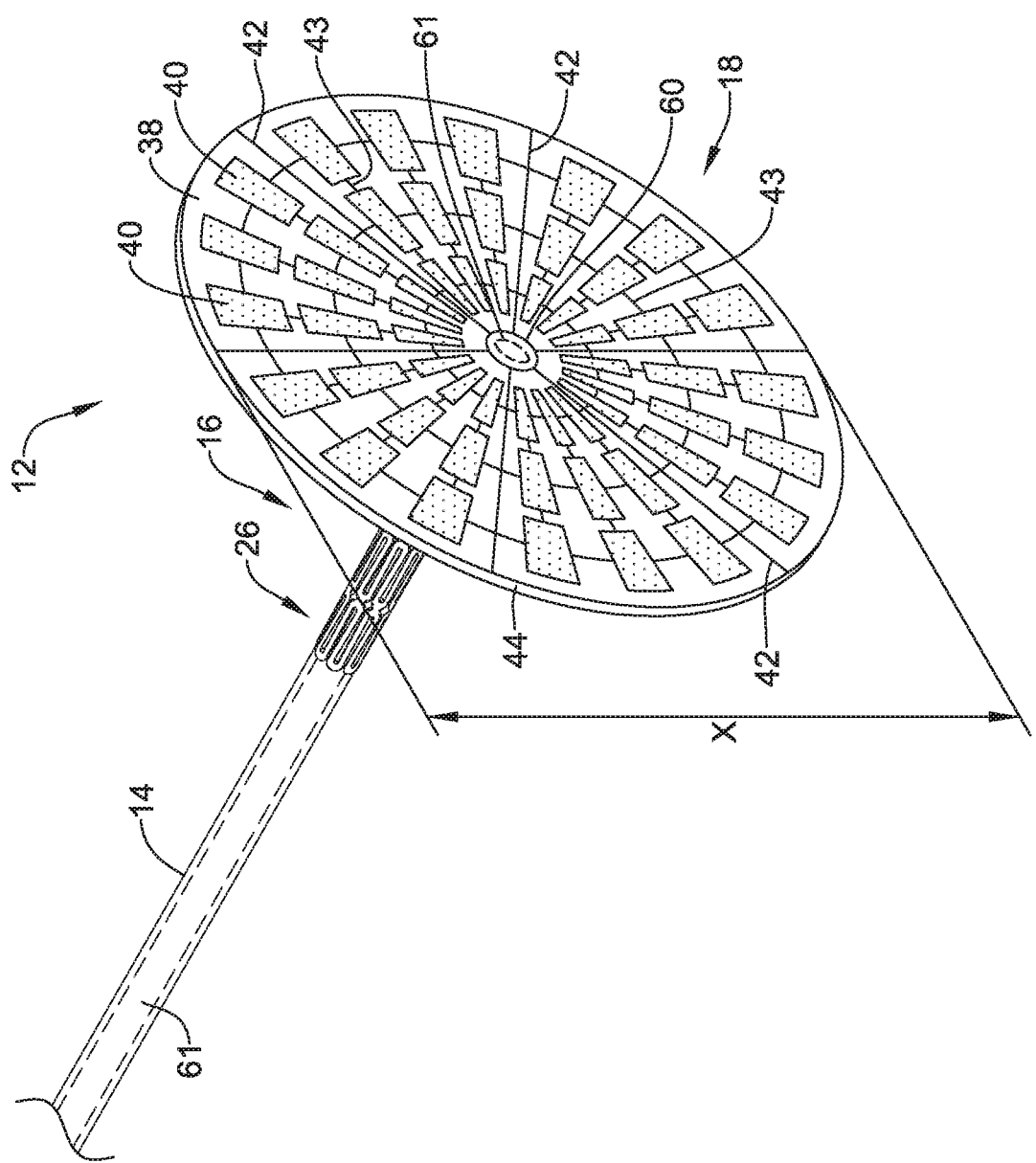
FIG. 8 illustrates another example medical device.

FIG. 8 illustrates the ablation device 12 described above whereby the ablation member 18 has been coupled to the expandable frame discussed with respect to FIGS. 2-6. Further, FIG. 8 illustrates the expandable frame 16 attached to a distal end of the shaft 14. It can be appreciated that FIG. 8 illustrates the expandable frame 16 in a configuration similar to the configuration of the frame 16 shown in FIG. 4, FIG. 5 and FIG. 6 (e.g., a configuration in which the expandable portion 28 of the frame is substantially flat or substantially convex relative to the base member 26).

As illustrated in FIG. 8, when in an expanded configuration, the ablation electrodes 40 may face away from the base member 26, thereby allowing the ablation electrodes to be directed toward and/or contact tissue. While not shown specifically in FIG. 8, it can be appreciated that the ablation electrodes 40 may be electrically coupled (via the trace wires 43, for example) to a processing system (not shown in FIG. 8). As discussed above, a signal wire (not shown) may be electrically coupled to each ablation electrode 40 on the ablation member 18. The signal wires may extend through the lumen of shaft 14 and electrically couple each ablation electrode 40 to a processing system. When activated, the signal wires may carry an electrical signal to each of the ablation electrodes 40, thereby allowing the ablation electrodes to delivery ablation energy to the target tissue. It is contemplated that, when activated during an ablation procedure, the ablation electrodes 40 may not only ablate tissue, but may also cauterize the target tissue.

It can be appreciated that, in some examples, the ablation member 18 may be disposed along and/or attached to the inside surface of the entire frame 16 or along only a portion of the inside surface of the frame 16. In other words, the ablation member 18 may cover the entire inside surface area of the frame 16 or may cover only a portion of the inner surface of the frame 16. In other words, the ablation member 18 may cover only selected portions of the frame 16, thereby creating portions of the frame 16 which are free from the ablation member 18.

Additionally, in some instances, a portion of the ablation member 18 may "wrap around" the outer perimeter 44 (e.g., the distal ends of the peaks 32) of the expandable frame 16. In other words, in some instances, the ablation member 18 may extend from a position in which the ablation member 18 contacts the inner surface of the frame 16 to a position in which the ablation member 18 contacts the outer surface of the frame 16. Further, in some examples, the ablation member 18 may include one or more "pockets" (not shown in FIG. 8) which are designed to permit one or more of the peaks 32 to be inserted therein. It can be appreciated that the pockets may be designed to couple (e.g., secure) the ablation member 18 to the frame 16.

As described above, FIG. 8 further illustrates a push/pull shaft member 61 disposed within the lumen of the shaft 14. The push/pull member 61 may extend through the frame 16 and be coupled to the ablation member 18. For example, FIG. 8 illustrates the push/pull member 61 may be attached to a central region 60 of the ablation member 18. As described above, actuation of the push/pull member 61 may change the shape and/or configuration of the ablation member 18. For example, as the push/pull member 61 is shifted in a proximal-to-distal direction, the ablation member 18 may shift from a relatively flat configuration to a substantially convex configuration. In other words, "pushing" the push/pull member 61 in a proximal-to-distal direction may push the central region 60 of the ablation member 18 in a distal direction, thereby bowing the ablation member 18 into a convex shape.

FIG. 8 further illustrates that the ablation member 18 may include an outer diameter "X." In some examples, diameter "X" may be about 5 mm to 55 mm, or about 10 mm to 45 mm, or about 15 to 40 mm, or about 20 mm to 35 mm, or about 25 mm to 30 mm. Further, in some examples, diameter "X" may be about 22 mm.

Figure 9:
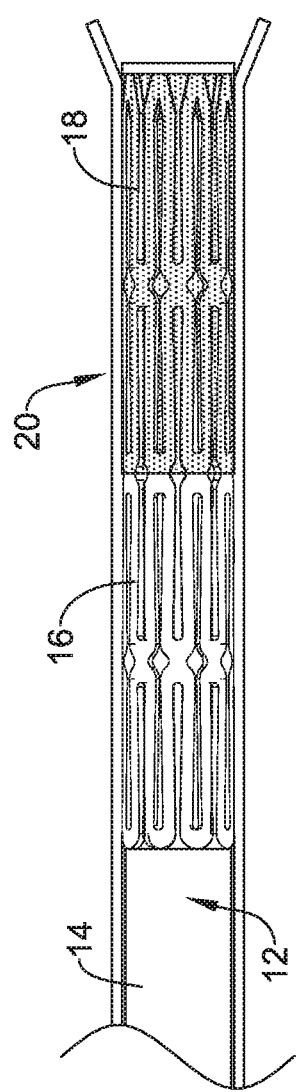
FIGS. 9-11 illustrate a series of steps showing an example medical being deployed from an example delivery catheter.
Figure 10:
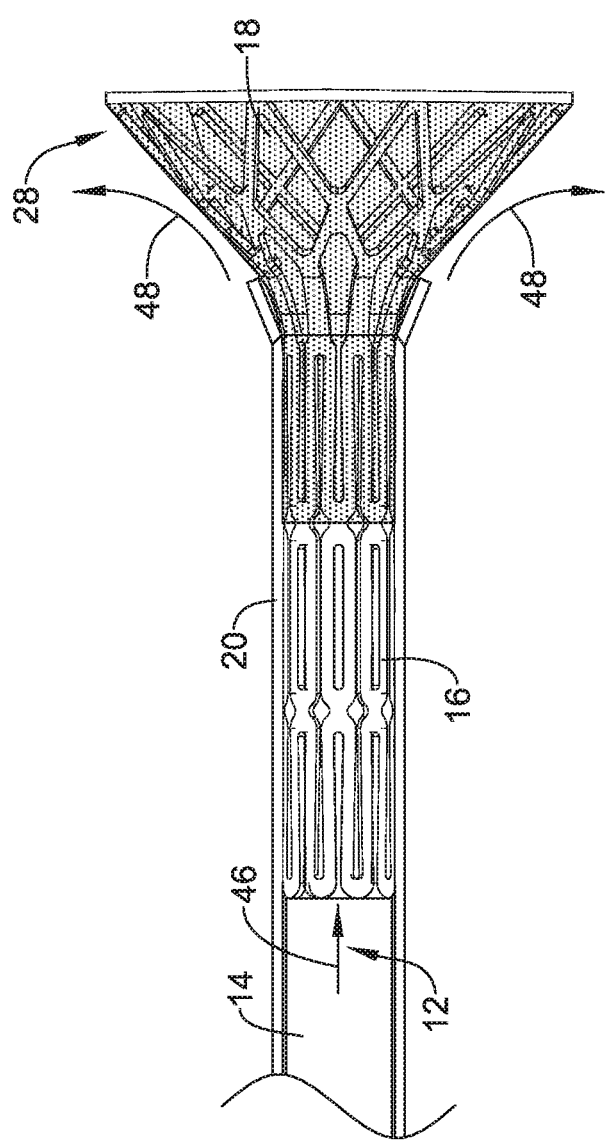
Figure 11:
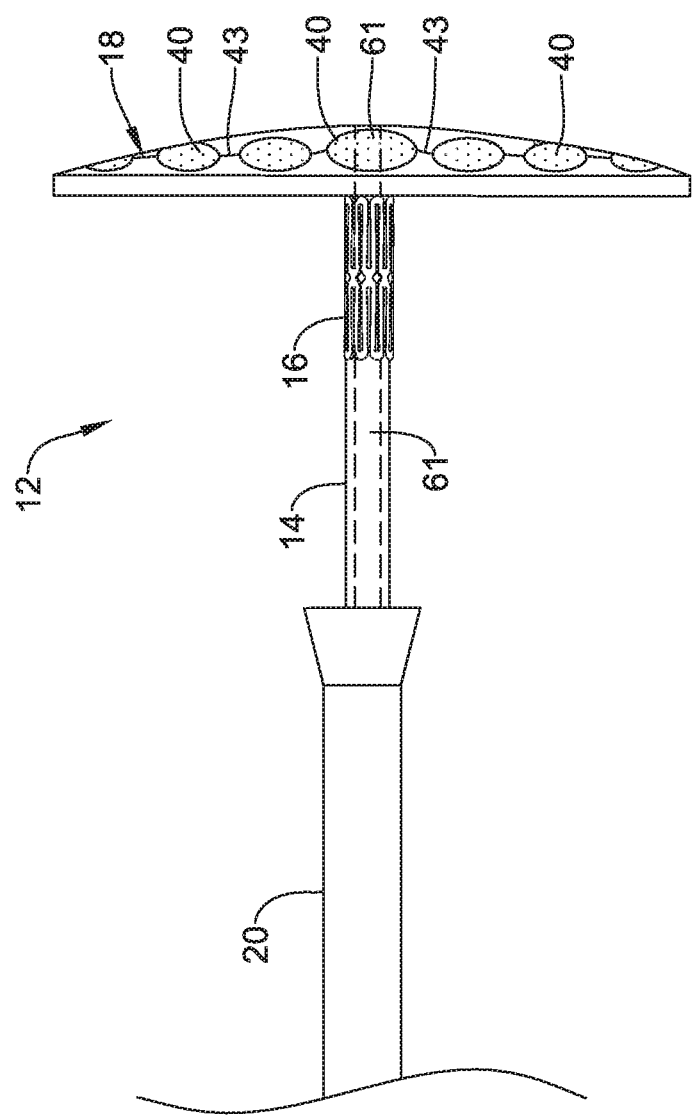

FIGS. 9-11 illustrate a series of steps showing the ablation device 12 being deployed from delivery configuration to a deployed configuration.

For example, FIG. 9 illustrates the ablation device 12 (including the frame 16 coupled to the shaft 14 and the ablation member 18 coupled to the expandable portion of the frame 16) positioned within the lumen of the delivery sheath 20. As shown in FIG. 9, the proximal end of the frame 16 may be attached to the distal end of the shaft 14. Further, it can be appreciated that, when in the delivery configuration, the ablation member 18 may be folded, rolled, pleated, etc. on itself in a compact configuration. In some examples, the ablation member may be folded along fold lines 42 (described above) to arrange the ablation member in a compact (e.g., delivery) configuration.

FIG. 10 illustrates that ablation device 12 being advanced in a proximal-to-distal direction (as depicted by the arrow 46). It can be appreciated that advancing the ablation device in a proximal-to-distal direction may be accomplished by manipulation of shaft 14 (e.g., via a hub member described above). Further, FIG. 10 illustrates the expandable portion 28 of the frame 16 expanding outward (as depicted by the arrows 48). As discussed above, as the expandable portion 28 of the frame 16 expands outward, the ablation member 18 may unfold such that the one or more ablation electrodes face away from the base member of the frame 16. It can be appreciated that the ablation member 18 may unfold along the fold lines 42. In some examples, it can be appreciated that the expansion and/or contraction of the ablation member 18 may resemble the folding and/or unfolding of a flower. In other words, the ablation member 18 may fold along fold lines 42 in a manner which wraps, pleats, layers, rolls, etc. the ablation member 18 upon itself.

FIG. 11 illustrates the ablation device 12 in a deployed configuration. As shown in FIG. 11, the ablation device 12 has been advanced out the distal end of the delivery sheath 20, and therefore, is free from the restraint of the delivery sheath 20. FIG. 11 illustrates that the expandable frame 16 has expanded such that the ablation electrodes 40 (coupled to one another via the electrical wires 43) of the ablation member 18 are facing away from the base member of the frame 16. It can be appreciated that the configuration of the ablation device 12 shown in FIG. 11 is similar to the configuration of the ablation device 12 shown in FIG. 1, whereby the ablation member 18 (and consequently the ablation electrodes 40) are configured to contact tissue.

Additionally, FIG. 11 illustrates the push/pull member 61 (discussed above) positioned such that the distal end region of the push/pull member 61 contacts and pushes (e.g., flexes) the ablation member 18 into a substantially convex shape. While FIG. 11 illustrates the push/pull member 61 positioning the ablation member 18 into a substantially convex shape, this is not intended to be limiting. Rather, it is contemplated that, in some examples, the push/pull member 61 may not be actuated to change the shape of the ablation member 18. For example, in some instances a clinician may opt to not actuate the push/pull member 61 (based upon the surface geometry of the target tissue site, for example). In other words, in some instances a clinician may choose to deploy the ablation member 18 into a substantially flat configuration (or any other configuration between a substantially configuration and a substantially convex configuration).

Figure 12:
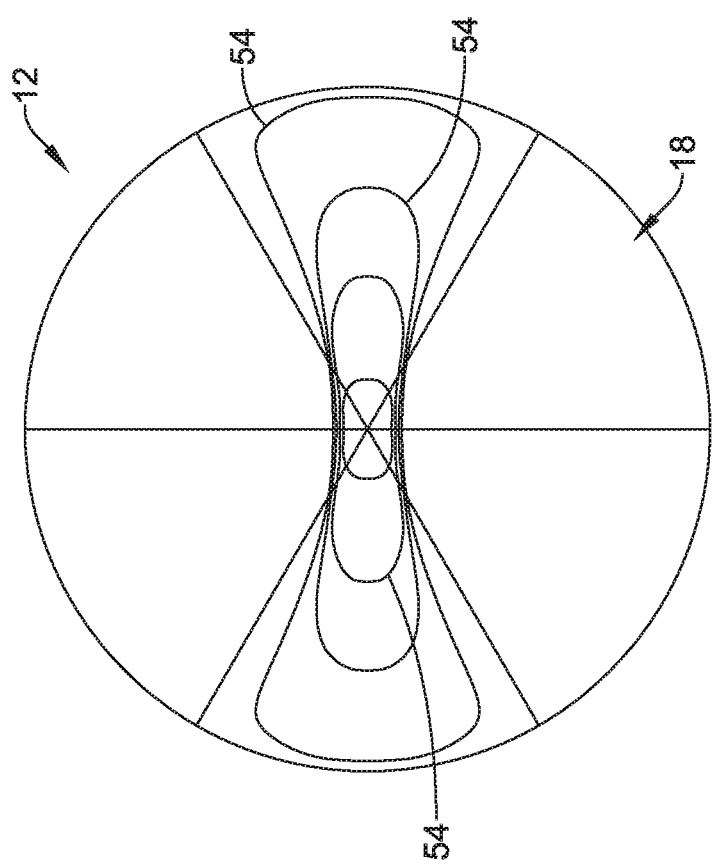
FIG. 12 illustrates an example ablation pattern of an example medical device.
Figure 13:
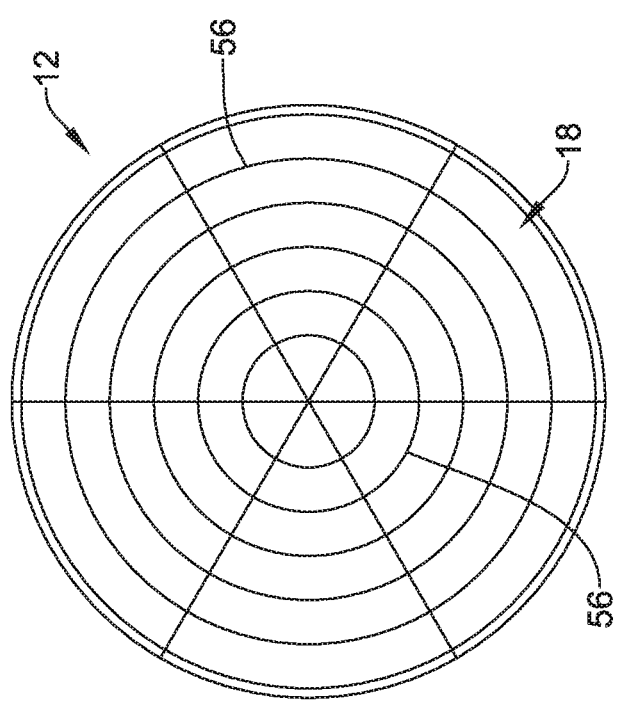
FIG. 13 illustrates another example ablation pattern of an example medical device.
Figure 14:
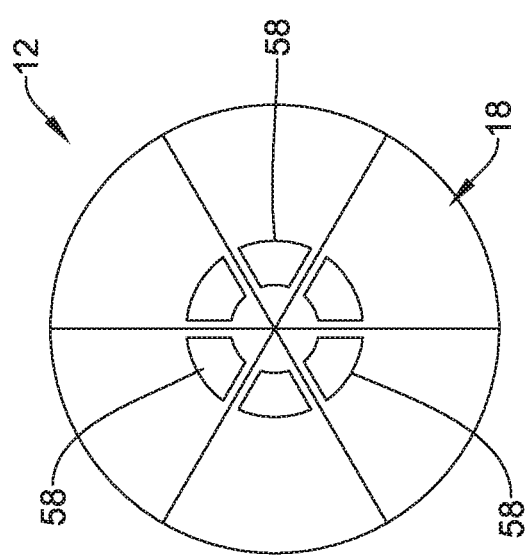
FIG. 14 illustrates another example ablation pattern of an example medical device.

As discussed above, in some examples it may be desirable to activate a specific number of ablation electrodes 40 such that they form a specific "ablation pattern" along the target tissue. In other words, the ablation device 12 may be designed such that a physician may be able customize the arrangement of ablation electrodes 40 utilized to ablate a target tissue site. FIGS. 12-14 illustrate several example ablation "patterns" which a physician may elect to utilize in an ablation procedure. For example, FIG. 12 illustrates and end view of the ablation device 12 in which the ablation member 18 is activated to form a "dog bone" activation pattern 54. FIG. 13 illustrates another example in which the ablation member 18 is activated to form a concentric circle ablation pattern 56. In yet another example, FIG. 14 illustrates another example in which the ablation member 18 is activated to form a dense activation pattern near the central region of the ablation member 18. It can be appreciated that the example ablation patterns illustrated in FIGS. 12-14 are not intended to be limiting. Rather, it is contemplated that the ablation device 12 may form a large variety of different ablation patterns.

Some example materials that can be used for the various components of the ablation device 12 or other components of ablation device 12 are described herein. However, this is not intended to limit the devices and methods described herein. Rather, it is contemplated that a variety of materials may be used for the various components of the ablation device 12 or other components of the ablation device 12 described herein.

The ablation device 12 and/or other components of the ablation device 12 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; copper; tin; silver; gold; combinations thereof; and the like; or any other suitable material.

In at least some embodiments, portions or all of the ablation device 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the ablation device 12 in determining its location. Some examples of radiopaque materials may include, but are not limited to, gold, platinum, palladium, tantalum, tungsten alloy, polymer material loaded with radiopaque filler, and the like. Additionally, other radiopaque marker bands and/or coils may also be incorporated into the design of the ablation device 12 to achieve the same result.

In some embodiments, a degree of Magnetic Resonance Imaging (MM) compatibility is imparted into the ablation device 12. For example, the ablation device 12, or portions thereof, may be made of a material that does not substantially distort the image and create substantial artifacts (e.g., gaps in the image). Certain ferromagnetic materials, for example, may not be suitable because they may create artifacts in an Mill image. The ablation device 12, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device, comprising:
    a catheter shaft including a distal end portion, wherein the distal end portion includes an ablation assembly, the ablation assembly including:
        an expandable frame comprising a unitary structure that includes a non-expandable base having a length and an expandable end region, the unitary structure of the expandable frame being defined by a plurality of interconnected struts that extend along the length of the non-expandable base and along the expandable end region, the plurality of interconnected struts defining a plurality of apertures along the expandable frame;
        wherein along the non-expandable base, the plurality of interconnected struts include a first strut and a second strut, wherein a portion of the first strut extends laterally and connects with the second strut; and
        an electrical circuit coupled to an inner surface of the expandable end region of the expandable frame, the electrical circuit including a plurality of ablation electrodes coupled thereto;
    wherein the expandable end region of the expandable frame is designed to shift from a delivery configuration in which the plurality of ablation electrodes face inward from the inner surface of the expandable frame to an expanded configuration in which the plurality of ablation electrodes are disposed along a substantially planar region of the expandable frame, face away from the non-expandable base of the expandable frame and are configured to contact a target tissue.

2. The medical device of claim 1, wherein the electrical circuit includes a flex circuit.

3. The medical device of claim 2, wherein the flex circuit includes a plurality of leaflets, and wherein each of the plurality of leaflets includes one or more of the plurality of ablation electrodes.

4. The medical device of claim 3, wherein the flex circuit includes a plurality of fold lines, and wherein each of the plurality of fold lines extends from a perimeter of the flex circuit to a center portion of the flex circuit.

5. The medical device of claim 4, wherein each of the plurality of leaflets is separated by one of the plurality of fold lines.

6. The medical device of claim 5, wherein the flex circuit is configured to unfold along one or more of the plurality of fold lines when the expandable frame shifts from the delivery configuration to the expanded configuration.

7. The medical device of claim 2, wherein the flex circuit includes a diameter when in the expanded configuration, and wherein the diameter is between 10 mm and 45 mm.

8. The medical device of claim 4, wherein the flex circuit is designed to shift from the expanded configuration to the delivery configuration, and wherein the flex circuit is configured to unfold inward along the plurality of fold lines when shifting from the expanded configuration to the delivery configuration.

9. The medical device of claim 2, wherein the flex circuit includes a pocket formed therein, and wherein at least a portion of the expandable frame is designed to insert into the pocket.

10. The medical device of claim 2, wherein the plurality of ablation electrodes are designed to ablate the target tissue utilizing ablation processes selected from a group comprising hypothermic ablation, hyperthermic ablation and athermal ablation.

11. The medical device of claim 2, wherein the flex circuit forms a continuous surface when in the expanded configuration.

12. The medical device of claim 2, wherein the flex circuit is configured to span across two or more of the plurality of apertures of the expandable frame when in the expanded configuration.

13. A medical device, comprising:
    a catheter shaft including a distal end portion;
    an expandable scaffold coupled to the distal end portion of the catheter shaft, the expandable scaffold comprising a unitary structure that includes a non-expandable base and an expandable end region, wherein the unitary structure of the expandable scaffold is defined by a plurality of interconnected struts extending along a length of the non-expandable base and along the expandable end region, the plurality of interconnected struts defining a plurality of apertures along the expandable scaffold;
    wherein along the non-expandable base, the plurality of interconnected struts include a first strut and a second strut that includes a peripheral surface that extends toward and is attached to the first strut;
    an ablation pad coupled to the expandable end region of the expandable scaffold, the ablation pad including a plurality of ablation electrodes coupled thereto;
    wherein the expandable end region of the expandable scaffold is designed to shift from a delivery configuration in which at least a portion of the ablation pad is disposed along an inner surface of the expandable scaffold to an expanded configuration in which a distally-facing planar region of the ablation pad faces a target tissue site and is configured to contact the target tissue site.

14. The medical device of claim 13, wherein the ablation pad includes a flex circuit.

15. The medical device of claim 13, wherein the ablation pad includes a plurality of fold lines, and wherein each of the plurality of fold lines extends from a perimeter of the ablation pad to a center portion of the ablation pad.

16. The medical device of claim 15, wherein the ablation pad is configured to unfold along one or more of the plurality of fold lines when the expandable scaffold shifts from the delivery configuration to the expanded configuration.

17. The medical device of claim 13, wherein the ablation pad forms a continuous surface when in the expanded configuration.

18. The medical device of claim 13, wherein the non-expandable base is substantially perpendicular to the expandable end region when in the expanded configuration.

19. A method of ablating tissue, the method comprising:
advancing an ablation catheter to a target tissue site, the ablation catheter including:
a catheter shaft including a distal end portion;
an expandable frame comprising a unitary structure that includes a non-expandable base and an annular expandable end region, the unitary structure of the expandable frame being formed from a plurality of interconnected struts extending along a length of the non-expandable base and along the annular expandable end region, the plurality of interconnected struts defining a plurality of apertures along the expandable frame;
wherein the plurality of interconnected struts are formed as the structure;
wherein along the non-expandable base, the plurality of interconnected struts include a first strut having a first side surface and a second strut having a second side surface that contacts and is attached to the first side surface; and
a flexible electric circuit coupled to an inner surface of the annular expandable end region of the expandable frame, the flexible electric circuit including a plurality of ablation electrodes coupled thereto; and
shifting the annular expandable end region of the expandable frame from a delivery configuration in which the plurality of ablation electrodes face inward from the inner surface of the expandable frame to an expanded configuration in which the plurality of ablation electrodes are disposed along a substantially planar region of the expandable frame, face away from the non-expandable base of the expandable frame and contact a target tissue.

20. The method of claim 19, the method further comprising advancing the expandable frame such that the plurality of ablation electrodes contact the target tissue.

* * * * *